US008540730B1

(12) United States Patent
Fernandez

(10) Patent No.: US 8,540,730 B1
(45) Date of Patent: Sep. 24, 2013

(54) SURGICAL INSTRUMENT FOR PERFORMING ELECTROSURGICAL PROCEDURES

(75) Inventor: Edgar Fernandez, Corona, CA (US)

(73) Assignee: Paul Tolen, Westminster, CA (US)

( * ) Notice: Subject to any disclaimer, the term of this patent is extended or adjusted under 35 U.S.C. 154(b) by 1547 days.

(21) Appl. No.: 11/768,162

(22) Filed: Jun. 25, 2007

(51) Int. Cl.
*A61B 17/50* (2006.01)
(52) U.S. Cl.
USPC .......................................................... 606/131
(58) Field of Classification Search
USPC ......... 606/80, 84, 85, 96, 129–132, 159–162, 606/167
See application file for complete search history.

(56) References Cited

U.S. PATENT DOCUMENTS

| 3,223,087 | A | * | 12/1965 | Vladyka et al. | 606/129 |
|---|---|---|---|---|---|
| 4,071,028 | A | | 1/1978 | Perkins | |
| D293,717 | S | * | 1/1988 | Proulx et al. | D24/189 |
| 5,167,640 | A | * | 12/1992 | Balding | 604/192 |
| D335,344 | S | * | 5/1993 | Hastings | D24/114 |
| 5,207,681 | A | * | 5/1993 | Ghadjar et al. | 606/96 |
| D372,309 | S | * | 7/1996 | Heldreth | D24/133 |
| 6,723,093 | B2 | | 4/2004 | Goth et al. | |
| 6,949,098 | B2 | | 9/2005 | Mulier et al. | |
| D572,820 | S | * | 7/2008 | Gallogly et al. | D24/130 |

* cited by examiner

*Primary Examiner* — Ryan Severson
(74) *Attorney, Agent, or Firm* — Robert M. Hunter

(57) ABSTRACT

A surgical instrument for performing electrosurgery is provided. The instrument includes an elongated body, an electrode blade tip, and a curettage tool removably attached to the instrument. The curettage tool has two scraping tips and each tip is positioned laterally from the electrode blade tip by a distance. The curettage tool has an attachment point configured for attaching to the tool or the electrode blade. The scraping tips of the curettage tool are disposed on two divergent arms that extend from the attachment point. The two scraping tips are disposed symmetrically relative to the electrode blade tip so that both left and right handed practitioners can use the instrument.

15 Claims, 3 Drawing Sheets

SURGICAL INSTRUMENT FOR PERFORMING ELECTROSURGICAL PROCEDURES

BACKGROUND OF THE INVENTION

1. Field of the Invention

The present invention relates generally to surgical instruments, and more particularly, relates to an instrument for performing electrosurgical procedures.

2. Description of the Related Art

Electrosurgical procedures are often used to remove and destroy superficial skin lesions such as pigmentation, viral warts, seborrheic keratoses, and skin tags. Various electrosurgical instruments have been developed to perform these procedures. One such widely used surgical instrument is manufactured by Conmed Corporation and sold under the trademark Hyfrecator. The Hyfrecator instrument is constructed with a single electrode blade disposed at a distal end of an electrosurgical probe. The electrode blade typically has a metal tip. In use, the metal tip is positioned in contact with the target tissue and a low voltage is applied to the electrode to deliver electric current through the tissue. The voltage dessicates the tissue and coagulates severed blood vessels at the treatment site. The dessicated tissue is then scraped off and removed with a curette, which is an instrument having a spoon shaped or looped tip. Because these steps are often repeated throughout a given procedure, the practitioner is required to switch back and forth between the electrosurgical instrument and the curette during the procedure. The constant switching of instruments can be inconvenient for the practitioner and decrease the efficiency of the procedure. Thus, it is an object of the present invention to overcome or ameliorate at least one of the disadvantages of the prior art, or to provide a useful alternative.

SUMMARY OF THE INVENTION

The preferred embodiments of the present invention have several features, no single one of which is solely responsible for their desirable attributes. Without limiting the scope of this invention, its more prominent features will now be discussed briefly. However, not all of the following features are necessary to achieve the advantages of the device. Therefore, none of the following features should be viewed as limiting. After considering this discussion, and particularly after reading the section entitled "Detailed Description of the Preferred Embodiments," one will understand how the features of the preferred embodiments provide advantages over prior art devices.

In one embodiment, the present invention provides a surgical instrument for performing electrosurgery and which is to be used in conjunction with an electrosurgical instrument. The instrument comprises an elongated body, an electrode blade coupled to a distal end of the elongated body, and a curettage tool having a plurality of scraping members. Preferably, the curettage tool is attached to the distal end of the elongated body in a manner such that the scraping members are positioned laterally from the electrode blade, wherein each scraping member is spaced apart from the tip portion of electrode blade by a first distance. In one implementation, the curettage tool further comprises two divergent arms, wherein the scraping members are disposed on the distal end of each respective arm. In another implementation, the scraping member has a loop configuration. In yet another implementation, the scraping members are disposed symmetrically about the electrode blade.

In another embodiment, the present invention provides a curettage tool adapted to couple with an electrosurgical instrument having an electrode tip. The tool comprises an attachment member adapted to couple the tool with the instrument, at least one divergent arm extending outwardly from the attachment member and a scraping member coupled to a distal end of each divergent arm. In one implementation, the distance between the scraping member and the electrode tip is between about 1 cm to 5 cm, preferably 3 cm. In another implementation, the angle between the longitudinal axis of each divergent arm and the longitudinal axis of the electrode tip is about 45°. In yet another implementation, the scraping member is laterally disposed relative to the electrode tip. In yet another implementation, the attachment member comprises a locking mechanism which locks the curettage tool in position relative to the electrosurgical instrument.

DETAILED DESCRIPTION OF THE PREFERRED EMBODIMENT

Figure 1:
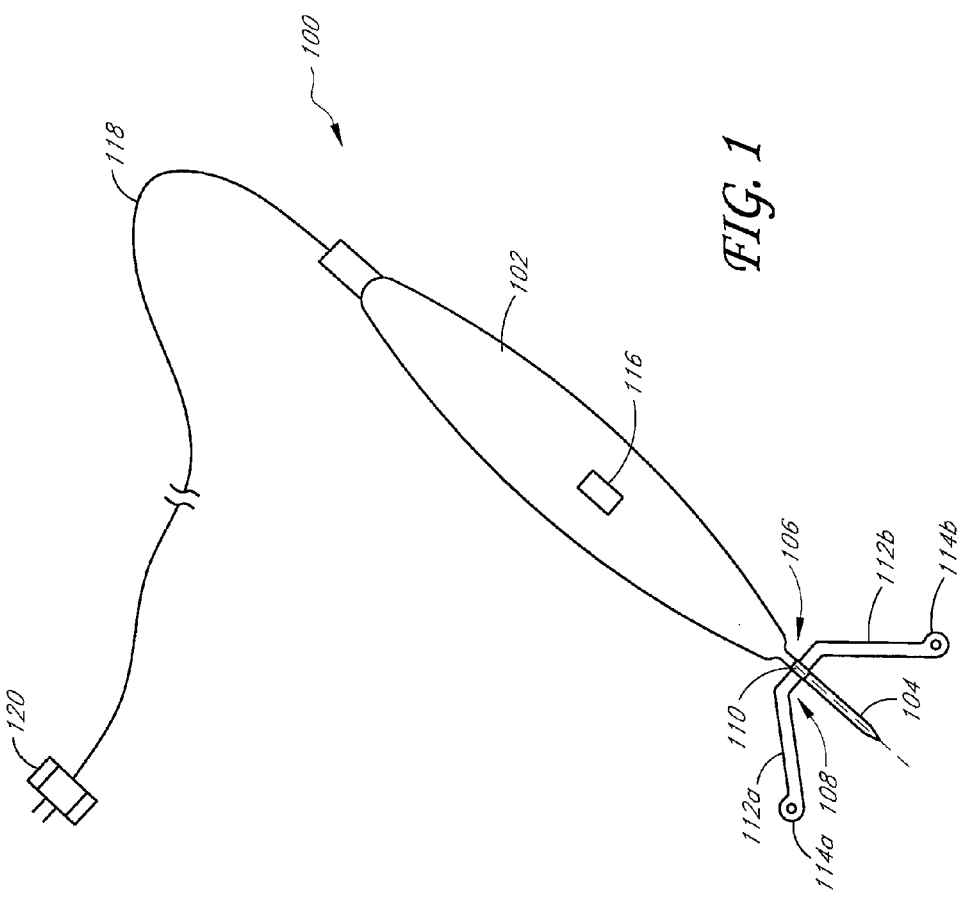
FIG. 1 is a schematic illustration of an electrosurgical instrument of one preferred embodiment of the presenting invention.

References will now be made to the drawings wherein like numerals refer to like parts throughout. FIG. 1 provides a schematic illustration of an electrosurgical instrument 100 of one preferred embodiment of the present invention. The electrosurgical instrument 100 is adapted for performing surgical procedures such as removing superficial skin lesions and pigmentations. As shown in FIG. 1, the electrosurgical instrument 100 generally comprises an elongated body 102, an electrode blade 104 extending from a distal end 106 thereof, and a curettage tool 108 coupled to and extending outwardly from a proximal end 110 of the electrode 104. In one embodiment, the curettage tool 108 has two outwardly extending arms 112a, 112b, each having a tip 114a, 114b adapted for scraping off and removing unwanted tissues from the treatment site. The curettage tips 114a, 114b can assume a variety of different configurations such as a loop configuration as shown in FIG. 1, a spoon configuration, or other curette configurations. In a preferred implementation, the curettage tip comprises a loop having a diameter of about 3 mm. In one embodiment, the curettage tool 108 is removably coupled to the electrode blade 104 or the instrument body 102 so that it can be replaced after each use. In other embodiments, the curettage tool 108 is fixedly coupled to the electrode blade 104 or instrument body 102.

As also shown in FIG. 1, the electrosurgical instrument 100 further includes an on-off switch 116, an electrical cord 118, and an electrical plug 120 for connecting the instrument to an external power source. The external power source is preferably an adjustable power source such as those sold by Birtcher having functionalities known in the art. In alternate embodiments, the electrosurgical instrument 100 is battery powered. When the instrument is powered, a low voltage is applied to the electrode to deliver electric current through the tissue at the treatment site, which dessicates the tissue and coagulates severed blood vessels in a manner known in the art. Additional details on the general operation and function of the electrosurgical instrument are disclosed in U.S. Pat. Nos. 5,226,904 and 6,117,109, which are hereby incorporated by reference in their entireties.

Figure 2:
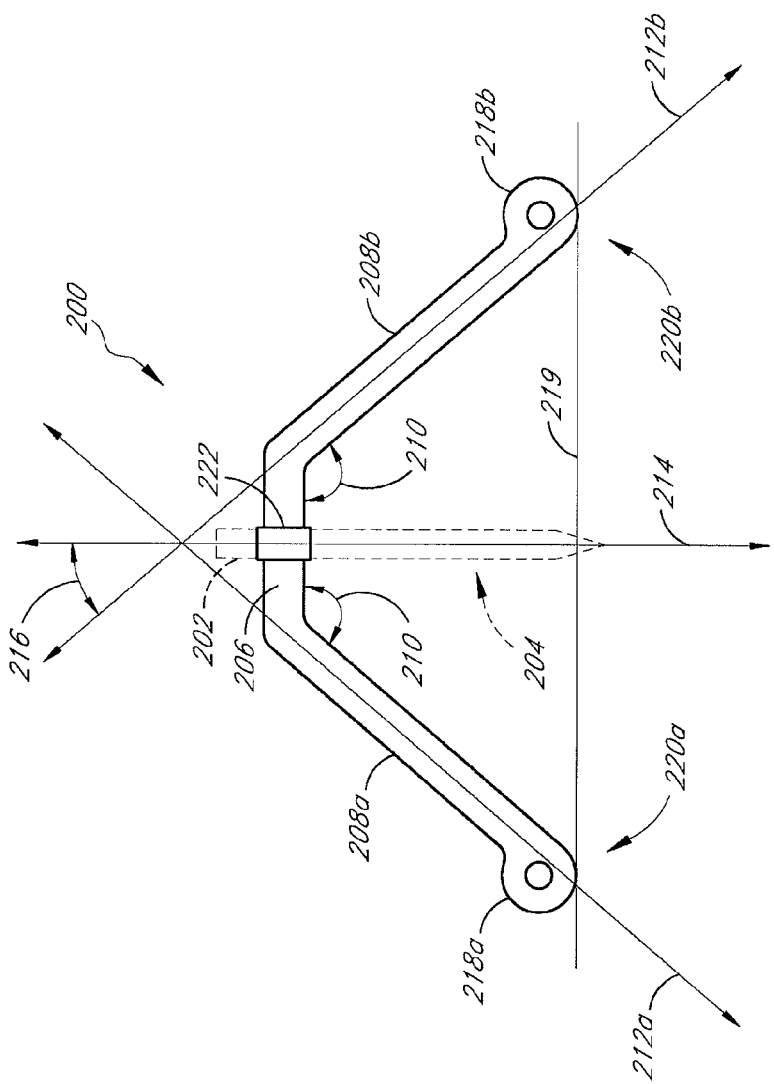
FIG. 2 is a schematic illustration of a curettage tool of one preferred embodiment that is removably attachable to the electrosurgical instrument of FIG. 1.

FIG. 2 provides a schematic illustration of a curettage tool 200 of one preferred embodiment of the present invention, which can be used in connection with an electrosurgical instrument such as the Hyfrecator device for removing superficial skin abnormalities. In this embodiment, the curettage tool 200 is designed to be removably attachable to the electrosurgical instrument. In one implementation, the curettage tool 200 is adapted to be removably attached to a shaft 202 which connects the body of the instrument to an electrode blade 204 shown in phantom lines.

As shown in FIG. 2, the curettage tool 200 has two diverging arms 208a, 208b, each extending outwardly from a horizontal section 206. Preferably, each arm 208a, 208b intersects the horizontal section 206 at an angle 210 greater than or equal to 90°. In one embodiment, the angle 210 is preferably between about 90°-150° degrees, more preferably between about 120°-140°, more preferably about 135°. Preferably, the longitudinal axis 212a, 212b of each divergent arm 208a, 208b intersects the longitudinal axis 214 of the electrode blade 204 at an angle 216 of about 45°. As also shown in FIG. 2, tip portions 218a, 218b of the curettage tool 200 are arranged in a manner such that the plane 219 defined by the bottom scraping surfaces 220a, 220b of the two tip portions 218a, 218b is substantially perpendicular to the longitudinal axis 214 of the electrode blade. Additionally, the distance between each tip portion 218a, 218b of the curettage tool and the tip of the electrode blade 204 is preferably between about 1 to 5 cm, more preferably about 3 cm. The unique angles and configuration of the curettage tool when used in connection with the electrode blade substantially maximize the use of the scalphoid or semi-lunar wrist joint rotation, which facilitates maneuvering of the instrument.

The curettage tool 108 further includes an attachment member 222 disposed midway in the horizontal section 206. The attachment member 222 is configured to removably attach the curettage tool 108 to the shaft 202 of the electrosurgical instrument. In one embodiment, the attachment member 222 comprises a passageway sized to form an interference fit with the shaft 202. In another embodiment, the attachment member 222 comprises a fastening device which allows the curettage tool to be clipped onto the shaft 202. It will be appreciated that numerous other fastening mechanisms can be used to removably attach the curettage tool to the electrosurgical instrument. In a preferred embodiment, the curettage tool along with the electrode blade can be locked in position relative to the electrosurgical instrument using methods known in the art. The locking mechanism advantageously prevents rotation of the curettage tool or the electrode blade. In a preferred embodiment, the curettage tool 108 is made of a plastic material and is disposable.

Figure 3:
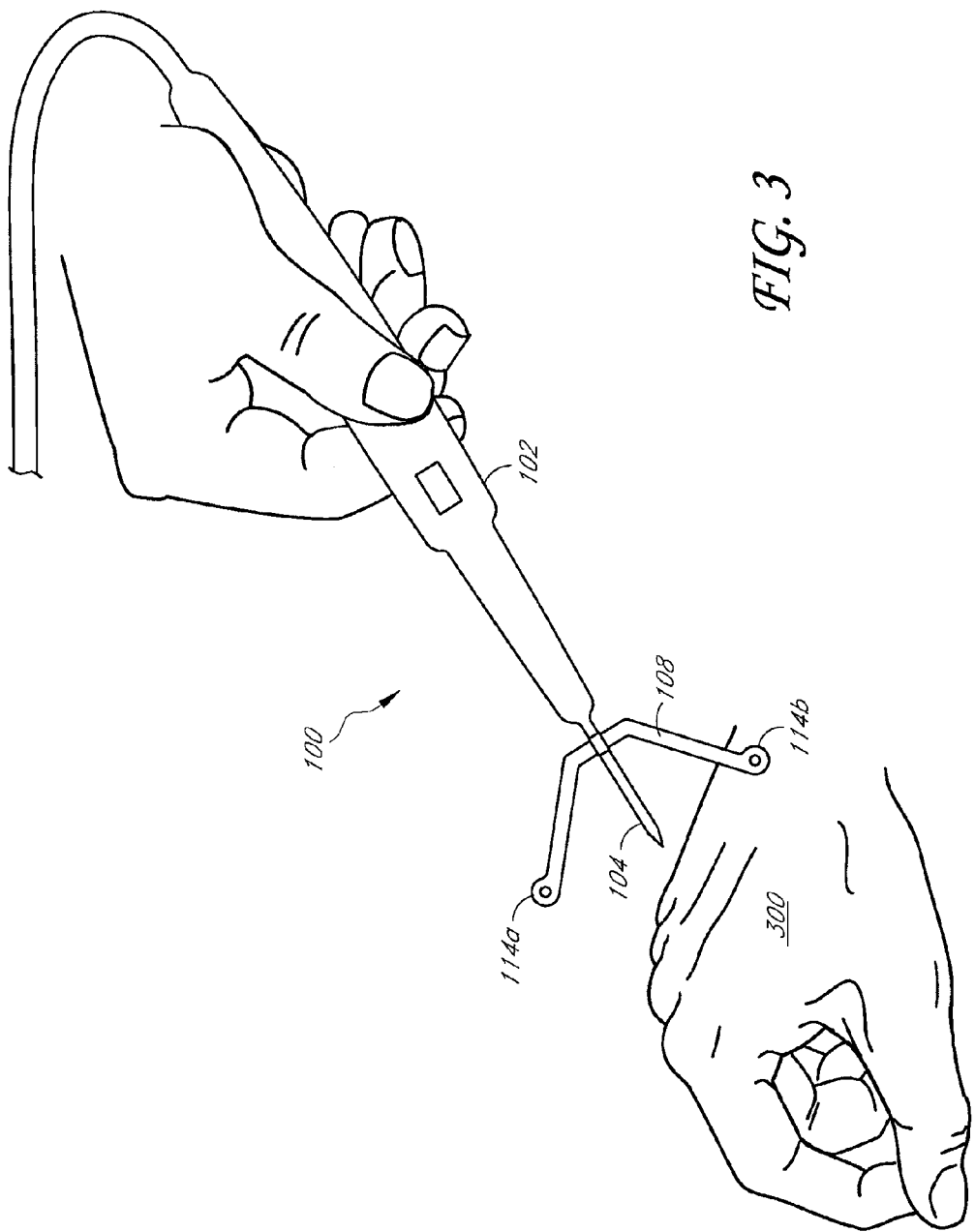
FIG. 3 illustrates the manner in which the electrosurgical instrument of FIG. 1 can be used to perform electrosurgical procedures.

FIG. 3 illustrates the manner in which the surgical instrument 100 shown in FIG. 1 can be used to perform an electrosurgical procedure. In practice, the operator holds the instrument 100 by the elongated body 102, which serves as a handle. After positioning the electrode blade 104 over a treatment site 300 and applying a voltage through the tissue at the treatment site to dessicate the tissue, the operator pivots the handle 102 very slightly to position one of the tips 114b of the curettage tool 108 over the treatment site to scrape off and remove the unwanted tissues and the like. After scraping away the tissues, the operator can pivot the handle 102 again to re-position the electrode blade 104 over the treatment site to continue the procedure. Advantageously, the curettage tool 108 is attached to the instrument in a manner so as to enable the operator to not have to constantly switch instruments during a procedure. Additionally, the unique angle of the curettage tool allows the hand to reach areas such as the alar area of the patient's nose. It also allows the operator to press the scraping tips of the curettage tool to the skin with just a few millimeters of movement. Further, the two diametrically opposing scraping tips on the curettage tool allow both right and left handed practitioners to use the device.

Although the foregoing description of the preferred embodiments of the present invention has shown, described and pointed out the fundamental novel features of the invention, it will be understood that various omissions, substitutions, and changes in the form of the detail of the invention as illustrated as well as the uses thereof, may be made by those skilled in the art, without departing from the spirit of the invention. Particularly, it will be appreciated that the preferred embodiments of the invention may manifest itself in other shapes and configurations as appropriate for the end use of the article made thereby.

What is claimed is:

1. A curettage tool adapted to couple with an electrosurgical instrument having a body, an electrode blade, and a shaft that connects the electrode blade to the body, the curettage tool comprising:
   an attachment member, said attachment member being adapted to removably couple the curettage tool with the shaft;
   a horizontal member projecting outwardly from the attachment member, said horizontal member having an end;
   a divergent arm extending outwardly from the end of the horizontal member; and
   a scraping member coupled to a distal end of the divergent arm;
   wherein the horizontal member and the divergent arm cooperate to position the scraping member at a fixed distance from the electrode blade when the curettage tool is coupled with the shaft.

2. The curettage tool of claim 1, wherein the fixed distance between the scraping member and the electrode blade is between about 1 to 5 cm when the curettage tool is coupled with the shaft.

3. The curettage tool of claim 1, wherein the angle between the longitudinal axis of the divergent arm and the longitudinal axis of the shaft is about 45° when the curettage tool is coupled with the shaft.

4. The curettage tool of claim 1, wherein the scraping member is laterally disposed relative to the electrode blade when the curettage tool is coupled with the shaft.

5. The curettage tool of claim 1, wherein the attachment member comprises a passageway adapted to form an interference fit with the shaft when the curettage tool is coupled with the shaft.

6. The curettage tool of claim 1, wherein the attachment member comprises a locking mechanism which locks the curettage tool in position relative to the electrosurgical instrument when the curettage tool is coupled with the shaft.

7. The curettage tool of claim 1, wherein the angle between the divergent arm and the horizontal member is greater than or equal to 90°.

8. The curettage tool of claim 1, wherein the angle between the divergent arm and the horizontal member is about 135°.

9. A curettage tool adapted to couple with an electrosurgical instrument comprising a body, an electrode blade, and a shaft that connects the electrode blade to the body, the curettage tool comprising:

an attachment member, the attachment member being adapted to releasably attach the curettage tool to the body, to the shaft, or to the electrode blade;

a horizontal section extending outwardly from the attachment member;

two divergent arms extending outwardly from the horizontal section;

a tip portion connected to a distal end of each divergent arm, each tip portion having a loop configuration and a bottom scraping surface;

wherein a plane defined by the bottom scraping surfaces is substantially perpendicular to the longitudinal axis of the electrode blade when the curettage tool is attached to the body, to the shaft, or to the electrode blade.

10. A curettage tool adapted to couple with an electrosurgical instrument comprising a body, an electrode blade, and a shaft that connects the electrode blade to the body, the curettage tool comprising:

an attachment member, the attachment member being adapted to attach the curettage tool to the body, to the shaft, or to the electrode blade;

an elongated horizontal member projecting outwardly from the attachment member;

a divergent arm extending outwardly from the elongated horizontal section;

a tip portion connected to a distal end the divergent arm, the tip portion comprising a curette;

wherein the longitudinal axis of the divergent arm intersects the longitudinal axis of the electrode blade at an angle of about 45° to the body, to the shaft, or to the electrode blade when the curettage tool is attached to the body, to the shaft or to the electrode blade.

11. A curettage tool adapted to couple with an electrosurgical instrument comprising a body, an electrode blade, and a shaft that connects the electrode blade to the body, the curettage tool comprising:

an attachment member, the attachment member being adapted to attach the curettage tool to the body, to the shaft or to the electrode blade;

a divergent arm extending outwardly from the attachment member;

a tip portion connected to a distal end of the divergent arm;

wherein the longitudinal axis of the divergent arm intersects the longitudinal axis of the electrode blade at an angle of about 45° when the curettage tool is attached to the body, to the shaft or to the electrode blade.

12. The curettage tool of claim 11 wherein the tip portion comprises a curette.

13. The curettage tool of claim 11 wherein the attachment member is fixed to the body, to the shaft, or to the electrode blade.

14. A curettage tool adapted to couple with an electrosurgical instrument comprising a body, an electrode blade, and a shaft that connects the electrode blade to the body, the curettage tool comprising:

an attachment member, the attachment member being adapted to attach the curettage tool to the body, to the shaft, or to the electrode blade;

a divergent arm extending outwardly from the attachment member;

a tip portion connected to a distal end of the divergent arm;

wherein the longitudinal axis of the divergent arm intersects the longitudinal axis of the electrode blade at an angle of about 45° when the curettage tool is attached to the body, to the shaft, or to the electrode blade;

wherein the tip portion has a loop configuration or a spoon configuration.

15. A curettage tool adapted to couple with an electrosurgical instrument comprising a body, an electrode blade, and a shaft that connects the electrode blade to the body, the curettage tool comprising:

an attachment member, the attachment member being adapted to attach the curettage tool to the body, to the shaft, or to the electrode blade;

a divergent arm extending outwardly from the attachment member;

a tip portion connected to a distal end of the divergent arm;

wherein the longitudinal axis of the divergent arm intersects the longitudinal axis of the electrode blade at an angle of about 45° when the curettage tool is attached to the body, to the shaft, or to the electrode blade;

wherein the tip portion is a loop having a diameter of about 3 mm.

* * * * *